(12) United States Patent
Velarde et al.

(10) Patent No.: US 8,030,521 B2
(45) Date of Patent: Oct. 4, 2011

(54) METHODS OF PRODUCING 1,3,5-TRIAMINO-2,4,6-TRINITROBENZENE

(75) Inventors: Stephen P. Velarde, Pleasant View, UT (US); Vincent E. Mancini, Omaha, NE (US)

(73) Assignee: Alliant Techsystems Inc., Minneapolis, MN (US)

( * ) Notice: Subject to any disclaimer, the term of this patent is extended or adjusted under 35 U.S.C. 154(b) by 1177 days.

(21) Appl. No.: 11/744,986

(22) Filed: May 7, 2007

(65) Prior Publication Data

US 2011/0172463 A1 Jul. 14, 2011

(51) Int. Cl.
 *C07C 209/18* (2006.01)
(52) U.S. Cl. ...................................... 564/399
(58) Field of Classification Search .................. 564/399
 See application file for complete search history.

(56) References Cited

U.S. PATENT DOCUMENTS

| | | | |
|---|---|---|---|
| 1,380,186 A | 5/1921 | Brewster |
| 1,396,001 A | 11/1921 | MacDonald |
| 2,246,963 A | 6/1941 | Wilkinson |
| 3,278,604 A | 10/1966 | Hoffman et al. |
| 3,394,183 A | 7/1968 | Dacons et al. |
| 3,933,926 A | 1/1976 | Salter et al. |
| 3,954,852 A | 5/1976 | Shen et al. |
| 4,032,377 A | 6/1977 | Benziger |
| 4,232,175 A | 11/1980 | Smith et al. |
| 4,434,304 A | 2/1984 | DeFusco, Jr. et al. |
| 4,745,232 A | 5/1988 | Schmitt et al. |
| 4,952,733 A | 8/1990 | Ott et al. |
| 4,997,987 A | 3/1991 | Ott et al. |
| 5,371,291 A | 12/1994 | Nader |
| 5,569,783 A | 10/1996 | Mitchell et al. |
| 5,633,406 A | 5/1997 | Mitchell et al. |
| 6,069,277 A | 5/2000 | Mitchell et al. |
| 7,057,072 B2 | 6/2006 | Mitchell et al. |
| 7,057,073 B2 | 6/2006 | Mitchell et al. |

FOREIGN PATENT DOCUMENTS

| | | |
|---|---|---|
| GB | 2355715 A | 5/2001 |
| GB | 2355714 | 3/2004 |
| WO | 9419310 | 9/1994 |

OTHER PUBLICATIONS

Agrawal, J.P., et al., Organic Chemistry of Explosives, pp. 142-143, © 2007, John Wiley & Sons Ltd., West Sussex, England.
Bellamy, A., et al., "Nitration of 1,3,5-trimethoxybenzene," J. Chem. Research (S), pp. 412-413, 2002.
Bellamy, A., et al., "Nitration of 1,3,5-trimethoxybenzene," J. Chem. Research (M), pp. 0919-0930, 2002.
Bellamy, Anthony J., et al., "A New Synthetic Route to 1,3,5-Triamino-2,4,6-Trinitrobenzene (TATB)," Propellants, Explosives, Pyrotechnics, vol. 27, pp. 49-58, 2002.
Bellamy, Anthony J., et al., "Synthesis of Ammonium Diaminopicrate (ADAP), a New Secondary Explosive," Propellants, Explosive, Pyrotechnics, vol. 27, pp. 59-61, 2002.
Bose, P.C., et al., "Occurrence of Dehydrorotenone in Derris uliginosa Benth," Indian J. Chem., vol. 14B, pp. 1012-1013, Dec. 1976.
DeFusco, A.A., et al., "An Improved Preparation of Trinitrophloroglucinol," Organic Preparations and Procedures Int., vol. 14, No. 6, pp. 393-424, 1982.
Dobratz, Brigitta M., "The Insensitive High Explosive Triaminotrinitrobenzene (TATB): Development and Characterization—1988 to 1994," Los Alamos Nat'l Lab., LA-13014-H, History, UC-741, 151 pages, Aug. 1995.
Dove, Michael F.A., et al., "Vanadium(v) oxytrinitrate, VO(NO3)3. A powerful reagent for the nitration of aromatic compounds at room temperature under non-acidic conditions," J. Chem. Soc., Perkin Trans. 1, pp. 1589-1590, 1998.
Hoffman, D. Mark, et al., "Comparison of New and Legacy TATBs," Journal of Energetic Materials, vol. 26, pp. 139-162, 2008.
Hofmann, K.A., et al., "Verbindungen von Kobaltnitriten mit p-Toluidin, Diazoaminotoluol, Hydrazin und Nitrosohydrazin," Miteilung a. d. Chem. Laborat. D. Kgl. Akad. D. Wissenschafter zu Munchen, Eingengangen am 14, Aug. 1908, pp. 3084-3090.
Maiti, A., et al., "Solvent screening for a hard-to-dissolve molecular crystal," Physical Chemistry Chemical Physics, vol. 10, pp. 5050-5056, 2008.
Majumdar, M.P., et al., "Nitration of Organic Compounds with Urea Nitrate-Sulphuric Acid," Indian J. Chem., vol. 14B, pp. 1012-1013, Dec. 1976.
Mehilal, et al., "Studies on 2,4,6-trinitrophloroglucinol (TNPG)—A novel flash sensitizer," Indian Journal of Engineering & Materials Sciences, vol. 11, pp. 59-62, Feb. 2004.
Mellor, John M., et al., "Improved Nitrations Using Metal Nitrate—Sulfuric Acid Systems," Tetrahedron, vol. 56, pp. 8019-8024, 2000.
Mitchell, Alexander R., et al., "A New Synthesis of TATB Using Inexpensive Starting Materials and Mild Reaction Conditions," prepared for submittal to the 27th International Annual Conference of ICT, Jun. 25-28, 1996, Karlsruhe, Federal Republic of Germany, 14 pages, Apr. 1996.
Olah, George A., et al., "New Synthetic Reagents and Reactions," Aldrichimica Acta, vol. 12, No. 3, pp. 43-49, 1979.
Olah, George A., et al., Nitration Methods and Mechanisms, © 1989 VCH Publishers, Inc., New York, NY, p. 29.

(Continued)

*Primary Examiner* — Brian J Davis
(74) *Attorney, Agent, or Firm* — TraskBritt

(57) ABSTRACT

Methods of producing TATB are disclosed. The method comprises providing acid wet TNPG and distilling water from the acid wet TNPG. The TNPG is reacted with an alkoxylating agent to form a solution of 1,3,5-trialkoxy-2,4,6-trinitrobenzene solution, which is reacted with an aminating agent. An alternate method comprises nitrating phloroglucinol in a first vessel to produce TNPG, which is reacted with an alkoxylating agent in a second vessel to form a solution comprising 1,3,5-trialkoxy-2,4,6-trinitrobenzene and at least one of at least one volatile byproduct and at least one nonvolatile byproduct. The at least one of at least one volatile byproduct and at least one nonvolatile byproduct is removed in situ. The 1,3,5-trialkoxy-2,4,6-trinitrobenzene is reacted with an aminating agent.

25 Claims, 4 Drawing Sheets

OTHER PUBLICATIONS

Ott, D.G., et al., "Preparation of 1,3,5-Triamino-2,4,6-Trinitrobenzene from 3,4-Dichloroanisole," Journal of Energetic Materials, vol. 5, pp. 343-354, 1987.

Schedule of 2008 GRC on Energetic Materials, 5 pages.

Schmidt, Robert D., et al., "New Synthesis of TATB. Process Development Studies," prepared for submittal to the JOWOG 9 (Joint Working Group 9), Aldermaston, England, Jun. 22-26, 1998, 14 pages, May 1998.

Smith, Bengt, "The Reaction between Phenols and Orthoesters. A New Synthesis of Aryl Alkyl Ethers," Acta Chem. Scand., vol. 10, No. 6, pp. 1006-1010, 1956.

U.S. Appl. No. 12/484,917, filed Jun. 15, 2009, entitled, "Methods for the Production of 1,3,5-Triamino-2,4,6-Trinitrobenzene".

U.S. Appl. No. 12/484,960, filed Jun. 15, 2009, entitled, "Methods for Nitrating Compounds".

U.S. Appl. No. 12/484,985, filed Jun. 15, 2009, entitled, "Methods of Producing 1,3,5-Triamino-2,4,6-Trinitrobenzene".

Waller, Francis J., et al., "Lanthanide(III) and Group IV metal triflate catalysed electrophilic nitration: 'nitrate capture' and the role of the metal centre," J. Chem. Soc., Perkin Trans. 1, pp. 867-871, 1999.

Zolfigol, Mohammad Ali, et al., "Nitration of Aromatic Compounds on Silica Sulfuric Acid," Bull. Korean Chem. Soc., vol. 25, No. 9, pp. 1414-1416, 2004.

Zolfigol, Mohammad Ali, et al., "Silica Sulfuric Acid/ NaNO2 as a Novel Heterogeneous System for the Nitration of Phenols under Mild Conditions," Molecules, vol. 7, pp. 734-742, 2002.

http://en.wikipedia.org/wiki/Room_temperature, Room Temperature, last modified Nov. 30, 2009, pp. 1-2.

METHODS OF PRODUCING 1,3,5-TRIAMINO-2,4,6-TRINITROBENZENE

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. N00174-03-C-0021 awarded by the Department of Defense.

TITLE OF THE INVENTION

1. Field of the Invention

Embodiments of the present invention relate to methods of producing 1,3,5-triamino-2,4,6-trinitrobenzene ("TATB") and, more particularly, to methods of producing TATB from phloroglucinol.

2. Background of the Invention

TATB is an insensitive energetic material used in various military applications. TATB is used in warhead fuzes and also as the explosive component in insensitive high explosives, such as in plastic bonded explosive compositions. TATB has been produced from various starting materials, such as 1,3,5-trichlorobenzene, 3,5-dichloroanisole, trinitrobenzene, picramide, or phloroglucinol, which is also known as 1,3,5-trihydroxybenzene. While various methods of producing TATB are known, TATB is no longer available from a qualified supplier for Department of Defense applications.

One method of synthesizing TATB from phloroglucinol is described in GB 2355715. The phloroglucinol is nitrated using sodium nitrite and nitric acid, forming trinitrophloroglucinol ("TNPG"), which is also known as 1,3,5-trihydroxy-2,4,6-trinitrobenzene. The nitric acid is added sequentially or in multiple additions. When cooled, a solid is produced, which is filtered, washed with 3 M hydrochloric acid ("HCl"), and dried, yielding a solid product that is a monohydrate of TNPG. The monohydrate of TNPG is a free-flowing solid. The TNPG is alkoxylated using a trialkyl orthoformate, such as triethyl orthoformate ("TEOF"), forming 1,3,5-triethoxy-2,4,6-trinitrobenzene ("TETNB"). The TNPG and TEOF are reacted with heat, forming TETNB, ethanol, and ethyl formate. The ethanol and ethyl formate are removed by distillation. The solution of TETNB is concentrated, yielding TETNB as a solid, which is recrystallized from ethanol. The purified TETNB is aminated using liquid ammonia, filtered, washed with N-methylpyrrolidinone and methanol, and dried, yielding crystals of the TATB. The TATB synthesis utilizes multiple drying and isolation acts to produce solid products of TNPG, TETNB, and TATB.

Since these intermediates are sensitive to impact, friction, or electrostatic discharge ("ESD"), or are otherwise dangerous to handle, it would be desirable to minimize exposure of personnel and equipment to the intermediates. In addition, it would be desirable to reduce the amount of labor and time needed to produce the TATB and to improve the purity of the TATB and TETNB.

BRIEF SUMMARY OF THE INVENTION

One embodiment of the present invention comprises a method of producing TATB. The method comprises providing acid wet TNPG and distilling water from the acid wet TNPG. The TNPG is reacted with an alkoxylating agent to form a solution of 1,3,5-trialkoxy-2,4,6-trinitrobenzene solution, which is reacted with an aminating agent.

Another embodiment of the present invention comprises a method of producing TATB that comprises nitrating phloroglucinol in a first vessel to produce TNPG. The TNPG is reacted with an alkoxylating agent in a second vessel to form a solution comprising 1,3,5-trialkoxy-2,4,6-trinitrobenzene and at least one of at least one volatile byproduct and at least one nonvolatile byproduct. The at least one of at least one volatile byproduct and at least one nonvolatile byproduct is removed in situ. The 1,3,5-trialkoxy-2,4,6-trinitrobenzene is reacted with an aminating agent in the second vessel.

Another embodiment of the present invention comprises a method of producing TATB comprising nitrating phloroglucinol to produce a reaction mixture comprising TNPG. The TNPG is exposed to an aqueous solution of hydrochloric acid to produce acid wet TNPG. Water is removed in situ, and the TNPG is reacted with TEOF to form a solution comprising TETNB. Byproducts from the solution comprising TETNB are removed in situ, and the TETNB is reacted with an aminating agent.

BRIEF DESCRIPTION OF THE SEVERAL VIEWS OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature, or method act indicates that such is contemplated for use in implementation of an embodiment of the invention and such term is used in preference to the more restrictive term "is" so as to avoid any implication that other compatible materials, structures, features, and methods usable in combination therewith should, or must be, excluded.

A method of producing TATB from phloroglucinol is disclosed. The method provides improved safety by reducing handling of hazardous or sensitive intermediates. The method also provides comparable or improved purity and yield of the intermediates and the TATB.

In one embodiment, phloroglucinol is nitrated to form TNPG, which is exposed to an aqueous, acidic solution. The term "acid wet TNPG" is used herein to refer to TNPG that has been exposed to the aqueous, acidic solution. As described below, the TNPG may be exposed to the aqueous, acidic solution to remove contaminants or may be stored in the aqueous, acidic solution to reduce its sensitivity to impact or ESD. After removing water, the TNGP is alkoxylated, forming a 1,3,5-trialkoxy-2,4,6-trinitrobenzene, which is aminated to produce the TATB. The removal of water and the alkoxylation and amination reactions are conducted in a single vessel. A reaction scheme for producing TATB from phloroglucinol is shown below:

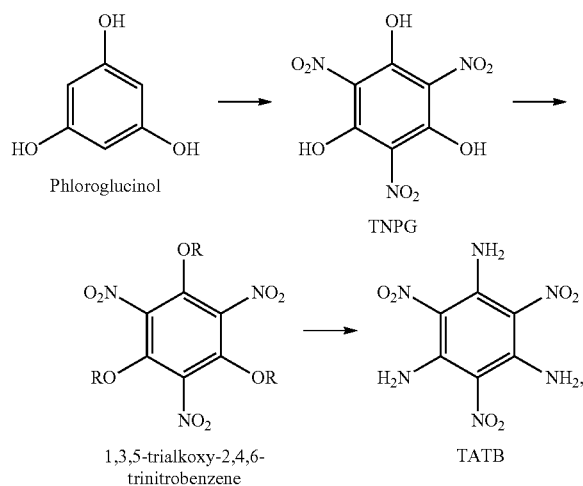

where R is an alkyl group including, but not limited to, a methyl, ethyl, or propyl group.

Figure 1:
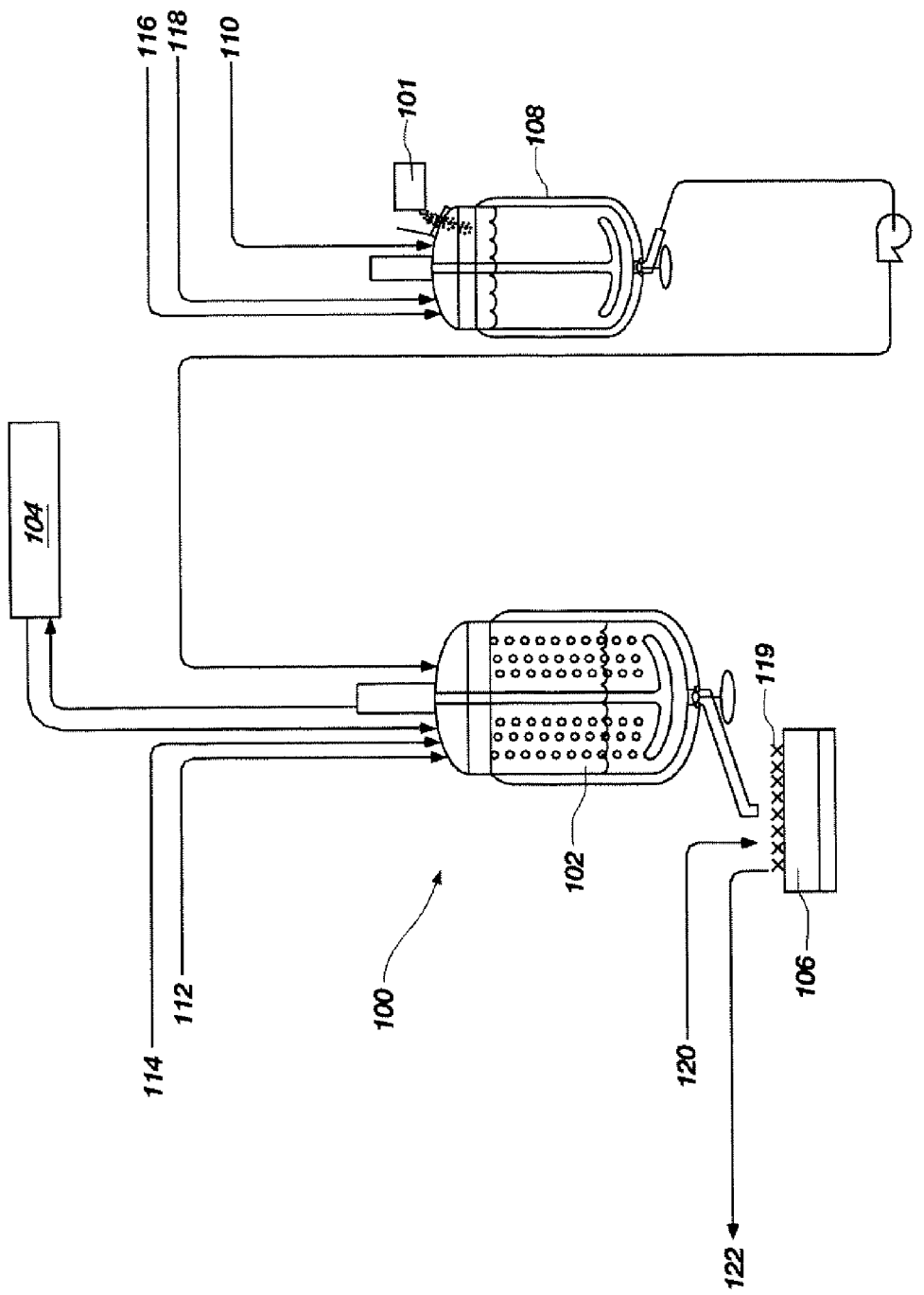
FIG. 1 is a flow diagram illustrating an embodiment of a system used to nitrate phloroglucinol.

The TNPG is produced by nitrating phloroglucinol. A first system 100 for nitrating the phloroglucinol 101 is shown in FIG. 1. The first system 100 includes a first vessel 102, distillation system 104, filter 106, and additional vessel 108. The additional vessel 108 is used to combine starting materials before their addition to the first vessel 102. The phloroglucinol 101 is nitrated using sodium nitrite 110, nitric acid 112, water 114, 116, and caustic solution 118. Phloroglucinol 101 is commercially available from various sources, such as from Sigma-Aldrich Co. (St Louis, MO), ACROS Organics/Fisher Scientific (Morris Plains, NJ), or Pechiney World Trade USA (Stamford, CT). The phloroglucinol 101 and sodium nitrite 110 are combined in the additional vessel 108 and slowly added to the nitric acid 112 located in the first vessel 102. Substantially all of the nitric acid 112 may be present in the first vessel 102 before adding the solution of phloroglucinol 101 and sodium nitrite 110. By using a single volume of the nitric acid 112, the complexity of the process is reduced, in addition to improving the yield and isolation of the TNPG. Using a single volume of the nitric acid 112 provides a TNPG yield of approximately 85% to approximately 90%. The nitration reaction may be conducted at a temperature within a range of from approximately −10° C. to approximately 25° C., such as at less than or equal to approximately 5° C. The nitration reaction may be conducted at ambient pressure. The phloroglucinol 101 may also be nitrated using other nitrating reagents, such as dinitrogen pentoxide and sulfuric acid or nitric acid and sulfuric acid. The distillation system 104 is operably coupled to first vessel 102.

In comparison, the TNPG yield when nitric acid is added sequentially (as described in GB 2355715) was 70%-75%. Without being bound to a particular theory, it is believed that the single addition of the nitric acid reduces or prevents the formation of a thick paste, as formed during the sequential acid addition described in GB 2355715. The thick paste produced by the sequential acid addition does not facilitate heat transfer and may result in decomposition of much of the trinitrosophloroglucinol intermediate.

The nitration of the phloroglucinol 101 produces a reaction mixture or slurry of TNPG and contaminants, which may include nitrates or salts. The contaminants may include, but are not limited to, sodium nitrate or sodium nitrite. The nitration reaction is conducted in the first vessel 102, which is compatible with the reaction and process conditions, such as in a round-bottom flask or a reactor. For the sake of example only, when commercial quantities of the TATB are to be produced, the first vessel 102 may be a 5-, 50-, or 500-gallon Pfaudler type glass-lined reactor. In one embodiment, after nitration, the TNPG slurry is transferred to a second vessel 202 (shown in FIG. 2) to perform the remaining process acts. In another embodiment, the TNPG slurry is washed in the first vessel 102 to remove the contaminants (as described below) before transferring the TNPG slurry to the second vessel 202.

The reaction mixture may be heated to a temperature of less than or equal to approximately 50° C. to complete the oxidation of nitrosophloroglucinol species to TNPG. The TNPG slurry may be cooled to a temperature within a range of from approximately 0° C. to approximately 25° C., filtered, and washed. The TNPG slurry 119 is discharged onto the filter 106, such as an indexing vacuum belt filter ("IVBF") and washed with a first volume of the aqueous, acidic solution 120 to remove the contaminants. The aqueous, acidic solution may include from approximately 0.5% by weight ("wt %") to approximately 25 wt % of an acid. The TNPG has a low solubility in a dilute solution of the acid, which includes, but is not limited to, HCl, nitric acid, sulfuric acid, or hydrogen bromide. In one embodiment, the acid is HCl. The resulting acid wet TNPG may be substantially free of the contaminants. The TNPG slurry 119 is washed with a second volume of the aqueous, acidic solution, forming the acid wet TNPG 122. The acid wet TNPG 122 may be stored in a vessel, sealed bag, or other airtight container until the alkoxylation reaction is conducted. When stored as acid wet TNPG 122, the TNPG has reduced sensitivity to impact and ESD. As such, the TNPG may be safely handled and stored. For the sake of example only, the acid wet TNPG 122 may be stored in a minimum of approximately 20 wt % of the aqueous, acidic solution. However, the acid wet TNPG 122 may be stored in lower amounts of the aqueous, acidic solution to provide the reduced sensitivity to impact and ESD. The acid wet TNPG 122 is a so-called "clumpy" solid having a resemblance to wet sand.

Figure 2:
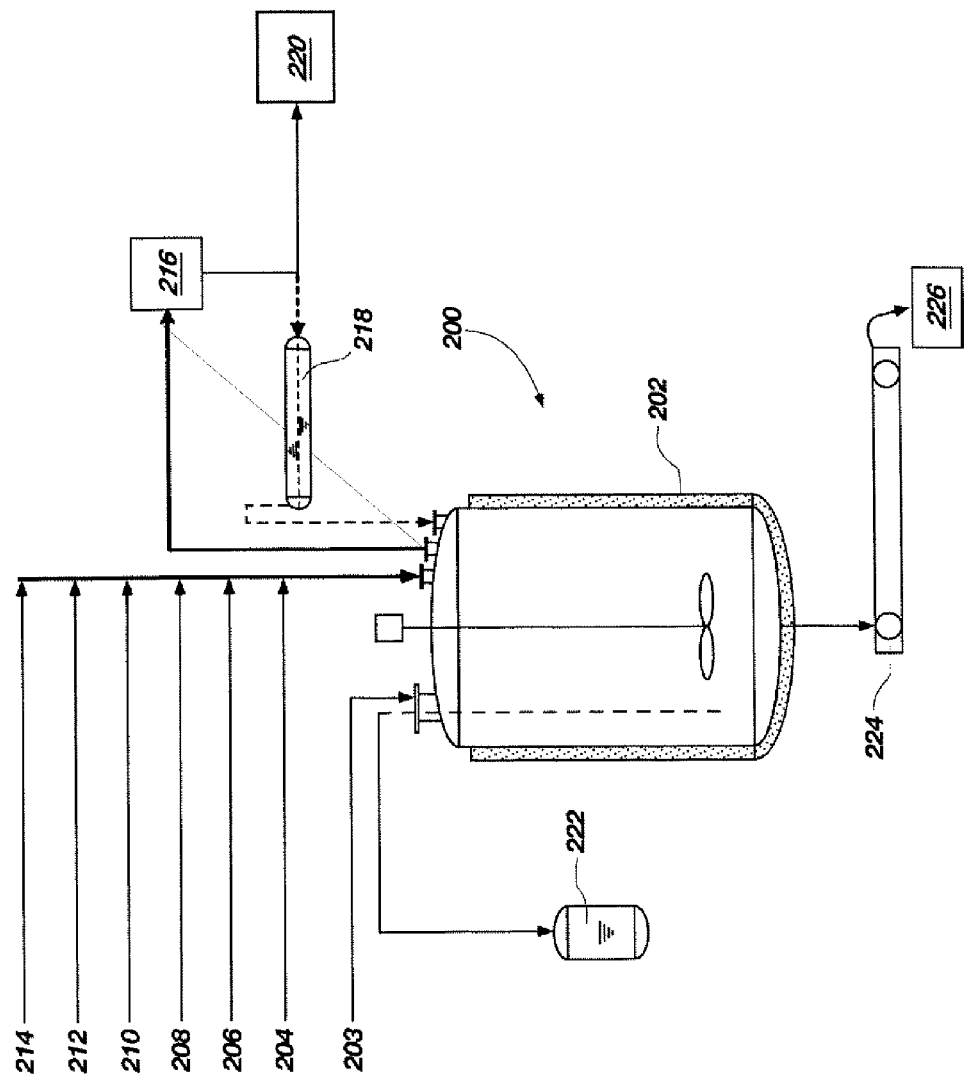
FIG. 2 is a flow diagram illustrating an embodiment of a system used to produce TATB from acid wet TNPG.

The acid wet TNPG 122 is transferred to a second system 200, as shown in FIG. 2, to remove water and to conduct the alkoxylation and amination reactions. The second system 200 includes the second vessel 202, inputs 203, 204, 206, 208, 210, 212, 214, distillation system 216, washing system 222, and filter 224. After introducing the acid wet TNPG 122 to the second vessel 202 through acid wet TNPG input 203, water is removed from the acid wet TNPG 122. An organic solvent is added to the acid wet TNPG 122, forming a slurry. The organic solvent may be introduced into the second vessel 202 through first organic solvent input 204. The organic solvent may be a nonpolar organic solvent including, but not limited to, toluene, a xylene, mesitylene, or heptane. Substantially all of the water is removed from the slurry by azeotropic distillation, forming a TNPG/organic solvent suspension or slurry. In one embodiment, toluene is used to azeotropically distill the water. As such, the acid wet TNPG is dried (water removed) in situ in the second vessel 202. The azeotropic distillation may be conducted at ambient pressure, or under reduced pressure to reduce process time.

The azeotropic distillation may be conducted using distillation system 216, which may be a short path distillation system, a long path distillation system, a straight path distillation system, a falling film distillation system, or a wiped-film distillation system. The distillation system 216 is operably coupled to the second vessel 202. Distillates collected during the distillation may be disposed of as waste 220 or may be recycled to the second vessel 202 through separator 218. For the sake of example only, if toluene is distilled, toluene may be recycled to the second vessel 202.

The second vessel 202 is compatible with subsequent reaction and processing conditions, such as the temperature and pressure conditions used in the alkoxylation and amination reactions. The second vessel 202 may be one of the types of vessels previously described for the first vessel 102. If commercial quantities of the TATB are to be produced, the second vessel 202 may be a 5-, 50-, or 500-gallon Pfaudler type glass-lined reactor. Since the remaining reactions and isolation of the intermediates are conducted in the second vessel 202, handling of the intermediates is reduced or eliminated, which reduces exposure of personnel and equipment to the intermediates.

The TNPG is alkoxylated by adding an alkoxylating agent to the TNPG/organic solvent suspension or slurry. The TNPG is introduced to the second vessel 202 through alkoxylating agent input 206. In one embodiment, the alkoxylating agent is a trialkyl orthoformate, such as trimethyl orthoformate, TEOF, tripropyl orthoformate, or mixtures thereof. Alternatively, triethyl phosphite may be used as the alkoxylating agent. A sufficient amount of the alkoxylating agent is added to the TNPG/organic solvent suspension or slurry such that the alkoxylation reaction proceeds substantially to completion. For the sake of example only, from approximately 5 moles to approximately 12 moles of the alkoxylating agent may be added per mole of TNPG. Alkoxylating the TNPG forms a 1,3,5-trialkoxy-2,4,6-trinitrobenzene compound, which remains dissolved in the organic solvent and forms a 1,3,5-trialkoxy-2,4,6-trinitrobenzene/organic solvent solution. Additional organic solvent, such as toluene, may, optionally, be added through the first organic solvent input 204 to maintain the volume of organic solvent in the second vessel 202 such that the 1,3,5-trialkoxy-2,4,6-trinitrobenzene remains in solution. In one embodiment, TEOF is used as the alkoxylating agent and is reacted with the TNPG, producing TETNB. While the example described herein utilizes TEOF as the alkoxylating agent, trimethyl orthoformate or tripropyl orthoformate may be used to form 1,3,5-trimethoxy-2,4,6-trinitrobenzene or 1,3,5-tripropoxy-2,4,6-trinitrobenzene, respectively.

The alkoxylation reaction may be conducted in the second vessel 202 at a temperature within a range of from approximately 75° C. to approximately 120° C. If the temperature is significantly higher than approximately 120° C., such as greater than approximately 125° C., the alkoxylating agent may be volatilized before reacting with the TNPG. If the temperature is significantly lower than 75° C., such as less than approximately 70° C., the alkoxylation reaction may proceed too slowly to be economical. A low temperature may also cause insufficient amounts of volatile byproducts to be removed during the reaction. The alkoxylation reaction may be conducted at atmospheric pressure for a sufficient amount of time to achieve trialkoxylation of the TNPG. The alkoxylation reaction may also be conducted at reduced pressure if a lower reaction temperature is desired. The reaction time may vary depending on the reaction size. Progress of the alkoxylation reaction may be monitored by conventional techniques, such as by high pressure liquid chromatography ("HPLC") or by proton nuclear magnetic resonance ("proton NMR"). However, even if the TNPG is under-reacted, the alkoxylation reaction may achieve desirable yields. For the sake of example only, at a temperature of approximately 90° C. under-reaction of the TNPG may produce 1,3,5-trialkoxy-2,4,6-trinitrobenzene at a yield of approximately 95%.

The alkoxylation reaction also produces volatile and nonvolatile byproducts. The volatile byproducts may include, but are not limited to, ethanol, ethyl formate, ethyl acetate, diethyl ether, and mixtures thereof. During the alkoxylation reaction, the volatile byproducts are substantially removed from the 1,3,5-trialkoxy-2,4,6-trinitrobenzene/organic solvent solution by continuous distillation through distillation system 216. By continuously removing the volatile byproducts, the alkoxylation reaction proceeds to substantial completion. The alkoxylation reaction is considered complete when the 1,3,5-trialkoxy-2,4,6-trinitrobenzene/organic solvent solution achieves a temperature of at least approximately 91° C. for several hours and distillation of the volatile byproducts substantially stops.

After cooling the 1,3,5-trialkoxy-2,4,6-trinitrobenzene/organic solvent solution to a temperature within a range of from approximately 25° C. to approximately 50° C., multiple water additions or water washes are conducted in situ to remove the nonvolatile impurities and to react with excess (unreacted) alkoxylating agent. The water, such as deionized water, may be introduced to the second vessel 202 through in situ wash input 208 or water input 210. The nonvolatile impurities may include, but are not limited to, inorganic salts, such as sodium chloride or nitrate salts, or partially alkoxylated trinitrobenzene compounds, such as mono- or di-alkoxylated trinitrobenzene compounds. An excess of water may be added to the 1,3,5-trialkoxy-2,4,6-trinitrobenzene/organic solvent solution, such as greater than approximately six equivalents of water. To neutralize acidic species, such as the partially alkoxylated trinitrobenzene compounds, a caustic solution is used to wash, in situ, the 1,3,5-trialkoxy-2,4,6-trinitrobenzene/organic solvent solution. The caustic solution may be introduced to the second vessel 202 through in situ wash input 208. The caustic solution may be an aqueous solution that includes from approximately 0.5% to approximately 5.0% of a caustic agent, such as sodium hydroxide ("NaOH"). However, other caustic agents, such as other metal hydroxides, may also be used including, but not limited to, potassium hydroxide, lithium hydroxide, sodium carbonate, sodium bicarbonate, potassium carbonate, or potassium bicarbonate.

The water also reacts with excess alkoxylating agent, producing the volatile byproducts mentioned above. The volatile byproducts remain in solution in the 1,3,5-trialkoxy-2,4,6-trinitrobenzene/organic solvent solution. The volatile byproducts may be removed by the distillation system 216.

Alternating water washes and caustic solution washes are conducted to remove substantially all of the nonvolatile impurities and the excess alkoxylating agent. Aqueous layers produced by the water washes and the caustic solution washes contain the nonvolatile impurities and the unreacted alkoxylating agent, which may be removed from the second vessel 202. Organic layers produced during the wash include the volatile byproducts. This in situ washing of the 1,3,5-trialkoxy-2,4,6-trinitrobenzene/organic solvent solution increases the washing efficiencies and the purity of the 1,3,5-trialkoxy-2,4,6-trinitrobenzene compared to external crystal washing. As a result, the purity of the TATB is also increased.

These water washes or water rinses may be conducted using a washing system 222, such as a conventional liquid:liquid washer or separator. For the sake of example only, co-current liquid:liquid washers, co-current liquid:liquid separators, counter current liquid:liquid washers, counter current liquid:liquid separators, fixed bed liquid:liquid washers, fixed bed liquid:liquid separators, horizontal liquid:liquid washers, horizontal liquid:liquid separators, vertical liquid: liquid washers, vertical liquid:liquid separators, rotating liquid:liquid washers, rotating liquid:liquid separators, static liquid:liquid washers, or static liquid:liquid separators may be used. The washing system 222 may be operatively coupled to the second vessel 202.

Distillation of the volatile byproducts produced by the alkoxylation reaction or by reacting excess alkoxylating agent with water may be performed using the distillation system 216. If a long path distillation system is used, the volatile byproducts may be removed quickly and more efficiently, because distillates do not condense back into the reactor or second vessel 202. Organic volatile byproducts, such as ethanol, ethyl formate, ethyl acetate, or diethyl ether, may alternatively be removed by organic absorption or osmosis. For the sake of example only, activated carbon may be used to remove the organic volatile byproducts.

Water is, optionally, removed from the 1,3,5-trialkoxy-2, 4,6-trinitrobenzene/organic solvent solution before conducting the amination reaction. While water does not adversely affect the amination reaction, the water may be removed to reduce methanol:water absorption before conducting the amination reaction.

The 1,3,5-trialkoxy-2,4,6-trinitrobenzene/organic solvent solution is diluted in the second vessel 202 with additional organic solvent, such as at least one organic solvent that does not react with an aminating agent under the conditions of the amination reaction. The additional organic solvent may include from approximately 0% to approximately 100% of a nonpolar solvent and from approximately 0% to approximately 100% of a polar solvent. The nonpolar solvent may include, but is not limited to, toluene, xylene, mesitylene, a straight chain or branched alkane, or combinations thereof. The polar solvent may include, but is not limited to, a straight chain or branched alcohol, such as methanol, ethanol, propanol, isopropanol, or combinations thereof. The additional organic solvent may also be a chlorinated solvent, such as methylene chloride or dichloroethane, dimethyl sulfoxide ("DMSO"), dimethylfuran ("DMF"), pyridine, diethyl ether, tetrahydrofuran ("THF"), acetonitrile, water, or combinations thereof. In addition, combinations of the chlorinated solvent, DMSO, DMF, pyridine, diethyl ether, THF, acetonitrile, or water with at least one of the nonpolar solvent and the polar solvent may be used. In one embodiment, the additional organic solvent includes a mixture of toluene and methanol. The additional organic solvent may be introduced to the second vessel 202 through second organic solvent input 212.

The aminating agent is reacted with the diluted 1,3,5-trialkoxy-2,4,6-trinitrobenzene/organic solvent solution in the second vessel 202 to produce a reaction mixture of TATB. The aminating agent may be introduced to the second vessel 202 through aminating agent input 214. The diluted 1,3,5-trialkoxy-2,4,6-trinitrobenzene/organic solvent solution may be cooled to a temperature within a range of from approximately −5° C. to approximately 5° C. and the aminating agent flowed through the diluted 1,3,5-trialkoxy-2,4,6-trinitrobenzene/organic solvent solution. The aminating agent may be ammonia (liquid or gaseous) or ammonium hydroxide (aqueous ammonia). The flow rate of the aminating agent may range from approximately 0.01 pounds of aminating agent per hour per pound of the additional organic solvent to approximately 1.0 pounds of aminating agent per hour per pound of the additional organic solvent. For the sake of example only, the flow rate of the aminating agent may range from approximately 0.03 pounds of aminating agent per hour per pound of the additional organic solvent to approximately 0.04 pounds of aminating agent per hour per pound of the additional organic solvent. In one embodiment, the flow rate of the ammonia is from approximately 0.03 pounds of ammonia per hour per pound of methanol to approximately 0.04 pounds of ammonia per hour per pound of methanol. The aminating agent may be flowed through the diluted 1,3,5-trialkoxy-2,4,6-trinitrobenzene/organic solvent solution for a sufficient amount of time that a solid is produced.

Upon adding the aminating agent, the 1,3,5-trialkoxy-2,4,6-trinitrobenzene is ammonolyzed to TATB. However, to provide a substantially complete reaction, the TATB reaction mixture may be heated under pressure such that remaining 1-alkoxy-3,5-diamino-2,4,6-trinitrobenzene is converted to TATB and ammonium diaminopierate, which is the major side product of this process. The TATB reaction mixture may be heated to a temperature within a range of from approximately −33° C. to approximately 50° C., such as from approximately −25° C. to approximately 10° C. The pressure may range from approximately 1 pound per square inch ("psi") to approximately 200 psi. In one embodiment, the pressure ranges from approximately 40 psi to approximately 50 psi. The solids produced by the amination reaction are discharged from the second vessel 202 onto a filter 224, such as an IVBF. The solids are filtered and washed, such as with an aqueous wash solution. The aqueous wash solution may include an organic solvent, such as methanol, isopropanol, other alcohol, or other organic solvent. In one embodiment, the aqueous wash solution is a mixture of methanol and water. The TATB is then be dried (water removed), such as in a vacuum oven, producing crystals of the TATB 226.

The particle size and morphology of the TATB crystals is controlled by adjusting the flow rate of the aminating agent, such as the ammonia. The TATB produced by the above-mentioned method may have a particle size within a range of from approximately 0.1 µm to approximately 100 µm. For most military and civilian applications, TATB having a particle size within a range of from approximately 40 µm to approximately 60 µm is desired. The particle size of the TATB crystals follows a near-Gaussian distribution based on the flow rate of the aminating agent. Low and high flow rates of the aminating agent produce TATB having a small particle size, while intermediate ammonia flow rates produce TATB having a larger particle size. For the sake of example only, an ammonia flow rate within the above-mentioned range produces TATB having a particle size within a range of from approximately 40 µm to approximately 60 µm.

The TATB crystals may form tight agglomerates having a cauliflower-like morphology. In contrast, TATB crystals produced by conventional techniques form plates that agglomerate in stacks. The purity and yield of the TATB produced by the above-mentioned method is comparable or improved relative to that produced by conventional techniques. The TATB may be greater than approximately 96% pure, such as greater than approximately 98% pure. The yield of the TATB (based on TNPG) may be greater than approximately 90%.

By producing the TATB as described above, the sensitivity to impact, friction, and ESD of various intermediates, such as TNPG, is reduced. As such, the TNPG and other intermediates may be more easily and safely handled. In addition, isolating and handling the 1,3,5-trialkoxy-2,4,6-trinitrobenzene may be eliminated, which provides labor and time savings and reduces exposure to this hazardous intermediate. The overall purity of the TATB and the efficiency of producing the TATB may also be improved. Since the TATB is produced and isolated in two vessels, handling of, and exposure to, the intermediates is reduced or eliminated.

The TATB may be formulated into an explosive composition for use in military applications or in civilian applications, such as for deep oil well explorations or as a reagent to manufacture components for liquid crystal computer displays. The explosive composition may include the TATB and conventional ingredients including, but not limited to, at least one oxidizer, at least one nitramine or nitrocarbon, at least one fuel, or combinations thereof. Additional ingredients including, but not limited to, binders, processing aids, or plasticizers, may optionally be present. The explosive composition including the TATB may be formulated by conventional techniques, such as by pressing, casting, or extruding.

The following examples serve to explain embodiments of the present invention in more detail. These examples are not to be construed as being exhaustive or exclusive as to the scope of this invention.

EXAMPLES

Example 1

Synthesis of TATB from TNPG

TNPG (39.8 g (0.152 mol) was slurried in 60 ml of toluene in a 250-ml round-bottom flask equipped with an overhead stirrer and a short path condenser. TEOF (76.1 ml (0.457 mol) was added to the round-bottom flask and the round-bottom flask was heated to 80° C.-85° C. to distill the toluene. After distilling 55 ml of the toluene, an additional 76.1 ml of TEOF was added to the round-bottom flask. The distillation was continued until an additional 62 ml of distillate was collected. The heat was discontinued and the reaction stirred at 25° C. for 14-16 hours. Toluene (20 ml) was added to the round-bottom flask, which was heated to 35° C. to dissolve all solids. Water (28 ml) was added to the round-bottom flask and stirred for 10 minutes before withdrawing and discarding the aqueous layer. A 5% NaOH solution (28 ml) was added to the round-bottom flask and stirred for 10 minutes before withdrawing and discarding the aqueous layer. Water (28 ml) was added to the round-bottom flask and stirred for 10 minutes before withdrawing and discarding the aqueous layer. The remaining solution of TETNB and toluene was diluted with toluene (40 ml) and methanol (30 ml) and the reaction was cooled to −4° C. Ammonia gas was bubbled into the round-bottom flask for 2.5 hours and the reaction was stirred for 4 hours maintaining a temperature of 0° C.-10° C., producing TATB as a solid. The TATB was filtered and sequentially washed with methanol and water. The TATB was dried in a vacuum oven at 55° C., yielding 30.4 g (77.5% yield based on TNPG) of TATB.

Example 2

Synthesis of TATB from Phloroglucinol

Figure 3:
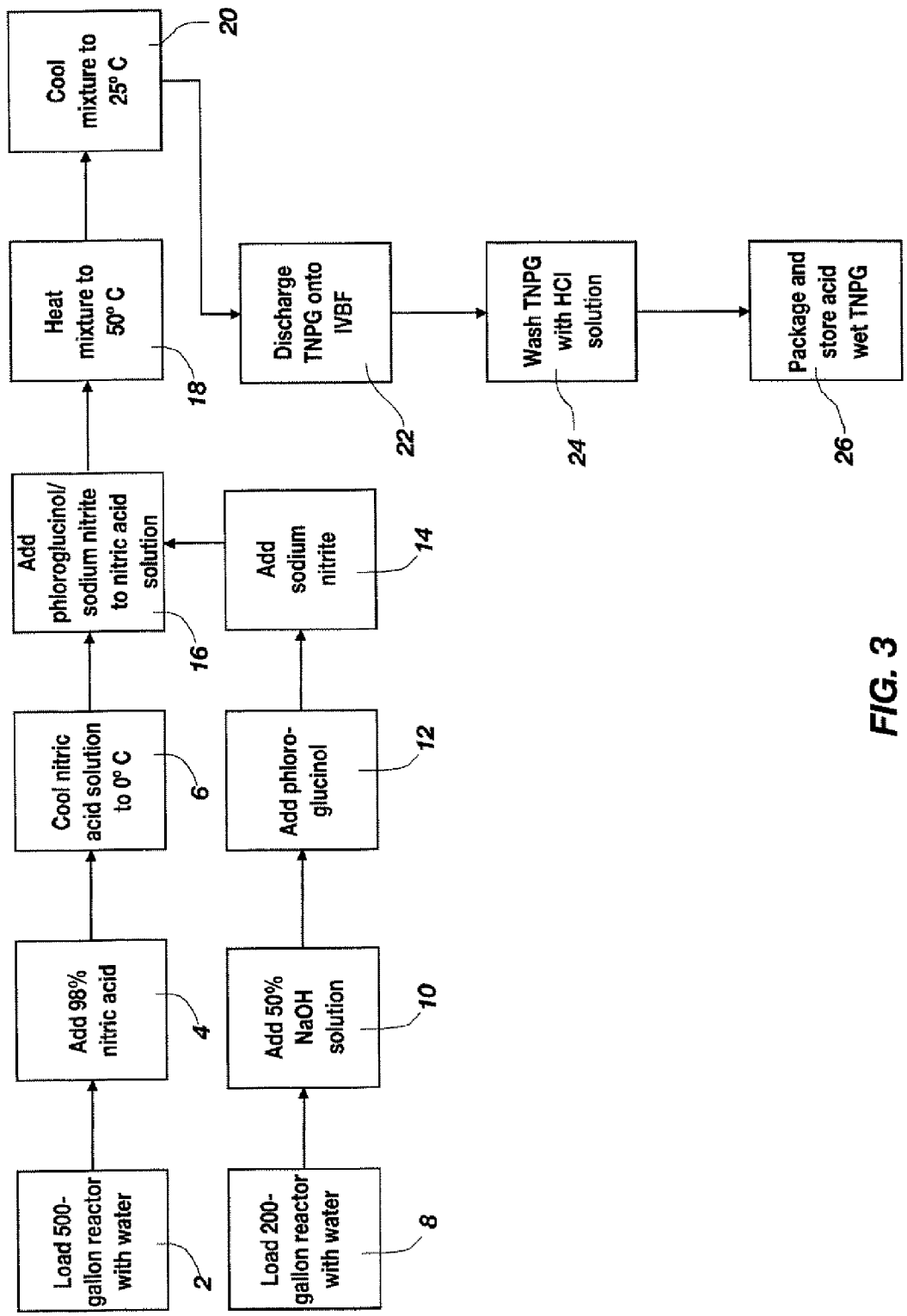
FIGS. 3 and 4 are block diagrams illustrating embodiments of a process flow for producing TATB from phloroglucinol.
Figure 4:
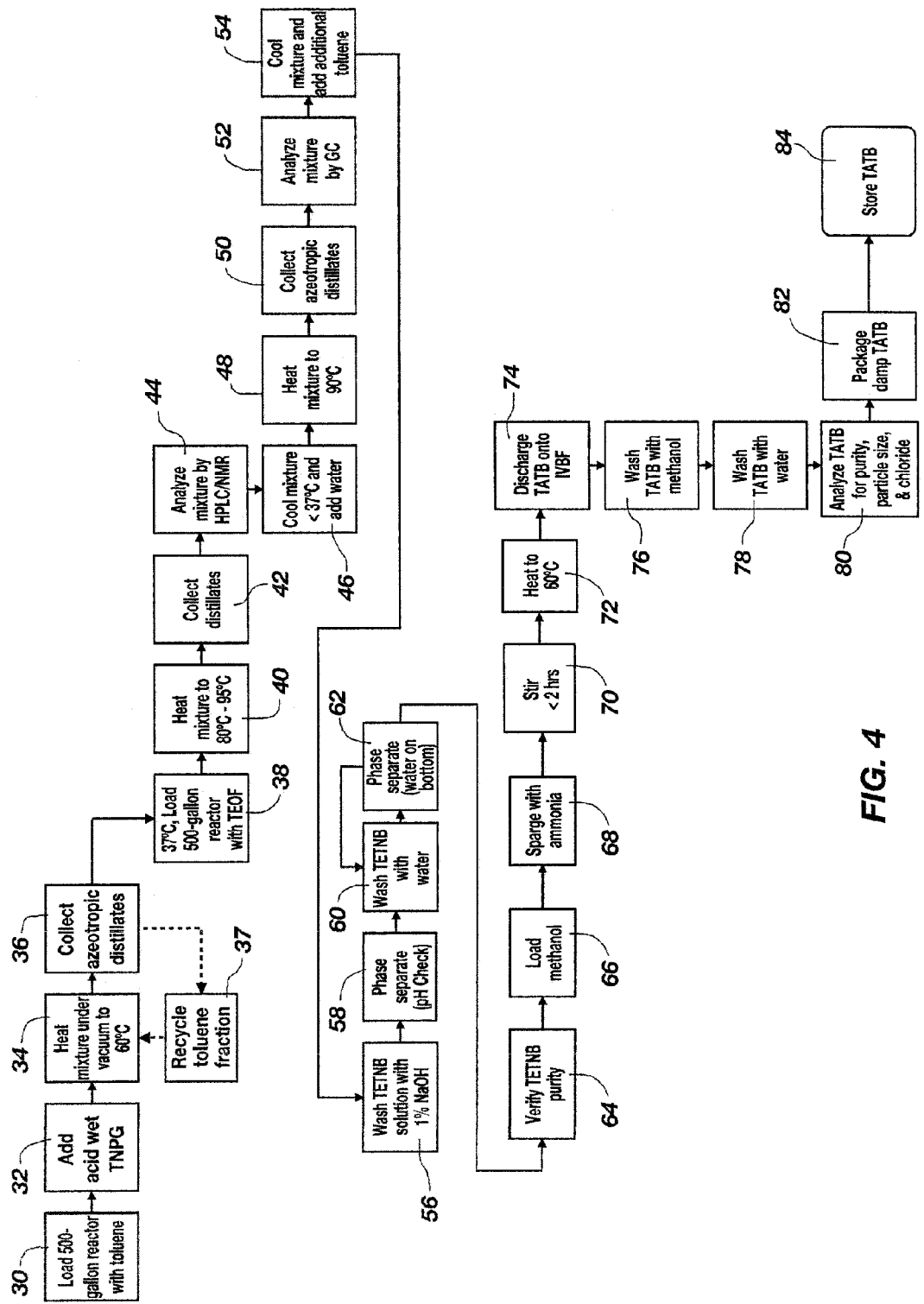

A process flow showing the synthesis of TATB from phloroglucinol is shown in FIGS. 3 and 4. FIG. 3 shows a process flow for nitrating phloroglucinol to produce TNPG and for forming the acid wet TNPG. As shown at 2 and 4, a 500-gallon, glass-lined Pfaudler reactor was charged with 150.3 gal (569 L) of deionized water and 88.3 gal (334 L, 7755 mol) of 98% (min. by analysis) nitric acid. The dilute nitric acid solution was stirred and cooled to a temperature between approximately −6.7° C. and approximately 4.4° C., as shown at 6. To a 200-gallon Pfaudler reactor was added 113 gal (428 L) of deionized water and 20.8 gal (79 L, 1467 mol) of a 50% sodium hydroxide solution, as shown at 8 and 10. Anhydrous phloroglucinol (203.3 lbs (92.3 kg, 732 mol)) was added, as shown at 12, and stirred to completely dissolve all solids. The sodium phloroglucinate solution was maintained below 30° C. and held for a maximum of 24 hours prior to addition of sodium nitrite. To the sodium phloroglucinate solution was added 445 lbs (202.1 kg, 2929 mol) of sodium nitrite, as shown at 14, with continued stirring. Upon complete dissolution of the solids, the solution in the 200-gallon Pfaudler reactor was fed into the cooled nitric acid solution in the 500-gallon reactor, as shown at 16, over a period of from approximately 13 hours to approximately 14 hours, maintaining the reaction temperature at or below approximately 4.4° C. during the addition. As shown at 18, the mixture was heated stepwise over a 7-hour period to complete the oxidation of the nitrosophloroglucinol species to TNPG. Stepwise heating was used to avoid excessive foaming. When the reaction temperature reached approximately 50° C., additional heating was discontinued, and the mixture was allowed a 30 minute dwell at the same temperature. As shown at 20, the mixture was cooled to near ambient (23° C.-27° C.) over a 3-4 hour period, at which point an aliquot was pulled and analyzed by HPLC to check for completion. Upon acceptance of the TNPG by HPLC, the reactor contents were discharged from the bottom discharge port onto an IVBF, as shown at 22, and spray washed with 65 gal of a 1% HCl solution, as shown at 24, producing acid wet TNPG. As shown at 26, the acid wet TNPG was packaged and sealed to prevent drying during storage. The average yield for four runs was 359.8 lbs of TNPG on a dry weight basis (85.4% yield).

FIG. 4 shows a process flow for the alkoxylation and amination reactions, which are conducted to produce TATB from the acid wet TNPG. As shown at 30 and 32, a 500-gallon, glass-lined Pfaudler reactor was charged with 148.3 gal (544.2 L) of toluene and 545 lbs (247.4 kg, 758 mol on a dry basis) of the acid wet TNPG (avg. 21.2% moisture). A condensate line to a heat exchanger was configured so that the water/toluene azeotrope was directed into an overflow, liquid: liquid separator ("LLS"). The LLS was charged with 35 gal (132.6 L) of so-called "make-up" toluene so that condensed toluene continuously flowed back into the reactor to prevent material from drying and caking. A mild vacuum was applied to the system, and heating was commenced to drive the distillation of the water/toluene azeotrope. The azeotrope was distilled/collected at 140° F. (60° C.), as shown at 34 and 36. As the composition of the azeotrope increased in toluene, the temperature of the distillate steadily increased. This temperature increase, along with visual cues (cessation of water droplet formation in the glass LLS, no increase in the quantity of water collected over time), enabled operators to terminate drying the acid wet TNPG and proceed with the alkoxylation reaction. The total azeotropic drying time was typically from 9 hours to 10 hours. Toluene collected from the distillation was recycled, as shown at 37.

As shown at 38, the vacuum was discontinued, the mixture was cooled to 37° C. and 200 gal (757L,4552mol) of TEOF was pumed into the 500-gallon Pfaudler reactor under the surface of the TNPG/toluene slurry to minimize vapor/flashing hazard associated with flammable and combustible liquids. The mixture was heated to drive the formation of TETNB, as shown at 40. The reaction by-products(ethanol, ethyl formate,diethl ether,and residual toluene) were collected at (atmospheric) distillation temperatures between 175° F. and 200° F. (between 80° C. and 95° C.) over a 14 hour to 16 hour period, as shown at 42. A slow nitrogen sweep was implemented to assist the distillation and assure that a vapor lock/reflux phenomenon was not encountered. Proton NMR and HPLC were used to monitor reaction progress, as shown at 44. When greater than approximately 97% conversion of TNPG to TETNB had been achieved, the mixture was cooled to below 37° C., and 26.1 gal (99 L, 5491 mol) of deionized water was pumped into the mixture to react with the remainder of the TEOF, as shown at 46. The mixture was heated at ambient pressure to drive the removal of the ethanol/ethyl formate by distillation (150° F. to 180° F.) and the distillates were collected, as shown at 48 and 50. This process typically took less than 12 hours. An indication that the majority of the ethanol/ethyl formate/water had been removed was a noticeable increase in the distillation temperature above 172° F. (78° C.). In addition, a clear separation in the distillate phases was noticeable as ethanol and ethyl formate were no longer present in the distillate to solubilize the toluene and water. Gas chromatography ("GC") was used to monitor reaction progress, as shown at 52. The mixture was cooled to ambient temperature and additional toluene was added to fully solubilize the TETNB, as shown at 54, as well as to provide a desired ratio of solvent to TETNB. As shown at 56, 58, 60, and 62, the toluene/TETNB solution was washed sequentially with 52 gallons of 1% NaOH, and two 52 gallon portions of deionized water. The wash solution was removed via stinger, and a pH check was conducted to ensure that the washes had a pH of greater than or approximately equal to 7. These washes removed unreacted/underreacted trinitrophloroglucinol species, and also removed excess salts from the nitration process. As shown at 64, HPLC was used to determine reaction purity, which was typically 100% TETNB.

Methanol (69.1 gal (262 L)) was pumped into the 500-gallon Pfaudler reactor, the TETNB solution was cooled to between 27° F. and 32° F. (between −3° C. and 0° C.), and anhydrous ammonia (206.5 kg, 12127 mol) was sparged into the reactor under the solution surface over a time period of between 33 hours and 34 hours, as shown at 66, 68, and 70. The reaction temperature was maintained at or below 37° F. (3° C.) during the ammonia feed. Upon completion of the ammonia addition, a TATB sample was withdrawn, and the reactor was sealed and heated to 122° F. (60° C.) for a minimum of 24 hours, as shown at 72. The reactor was slowly depressurized with cooling, the TATB discharged onto the IVBF, and the TATB washed sequentially with isopropanol (20.9 gal) or methanol and deionized water (103 gal), as shown at 74, 76, and 78. After analyzing the TATB for purity, particle size, and chloride content, the TATB was packaged damp in velostat or other appropriate bags, as shown at 80 and 82. Average TATB yield per reaction was 386 lbs (89.5% yield). The TATB was stored, as shown at 84.

While the invention may be susceptible to implementation with various modifications and in various forms, specific embodiments have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of producing 1,3,5-triamino-2,4,6-trinitrobenzene, comprising:
    providing acid wet trinitrophloroglucinol;
    distilling water from the acid wet trinitrophloroglucinol;
    reacting trinitrophloroglucinol with an alkoxylating agent to form a solution of 1,3,5-trialkoxy-2,4,6-trinitrobenzene; and
    reacting the 1,3,5-trialkoxy-2,4,6-trinitrobenzene with an aminating agent.

2. The method of claim 1, wherein providing acid wet trinitrophloroglucinol comprises exposing trinitrophloroglucinol to an acidic, aqueous solution.

3. The method of claim 2, wherein exposing trinitrophloroglucinol to an acidic, aqueous solution comprises exposing trinitrophloroglucinol to an aqueous solution comprising an acid selected from the group consisting of hydrochloric acid, nitric acid, sulfuric acid, and hydrogen bromide.

4. The method of claim 1, wherein providing acid wet trinitrophloroglucinol comprises exposing trinitrophloroglucinol to an aqueous solution comprising from approximately 0.5% by weight to approximately 25% by weight of hydrochloric acid.

5. The method of claim 1, wherein distilling water from the acid wet trinitrophloroglucinol comprises distilling, in situ, the water from the acid wet trinitrophloroglucinol.

6. The method of claim 1, further comprising removing, in situ, at least one of at least one volatile byproduct and at least one nonvolatile byproduct from the solution of 1,3,5-trialkoxy-2,4,6-trinitrobenzene.

7. The method of claim 6, wherein removing, in situ, at least one of at least one volatile byproduct and at least one nonvolatile byproduct from the solution of 1,3,5-trialkoxy-2, 4,6-trinitrobenzene comprises distilling, in situ, the at least one volatile byproduct.

8. The method of claim 6, wherein removing, in situ, at least one of at least one volatile byproduct and at least one nonvolatile byproduct from the solution of 1,3,5-trialkoxy-2, 4,6-trinitrobenzene comprises adding water to the solution of 1,3,5-trialkoxy-2,4,6-trinitrobenzene.

9. The method of claim 1, further comprising removing excess alkoxylating agent.

10. The method of claim 9, wherein removing excess alkoxylating agent comprises reacting, in situ, the excess alkoxylating agent with water.

11. A method of producing 1,3,5-triamino-2,4,6-trinitrobenzene, comprising:
    nitrating phloroglucinol in a first vessel to produce trinitrophloroglucinol;
    reacting the trinitrophloroglucinol with an alkoxylating agent in a second vessel to form a solution comprising 1,3,5-trialkoxy-2,4,6-trinitrobenzene and at least one of at least one volatile byproduct and at least one nonvolatile byproduct;
    removing, in situ, the at least one of at least one volatile byproduct and at least one nonvolatile byproduct; and
    reacting the 1,3,5-trialkoxy-2,4,6-trinitrobenzene with an aminating agent in the second vessel.

12. The method of claim 11, wherein nitrating phloroglucinol in a first vessel comprises adding phloroglucinol and sodium nitrite to a single volume of nitric acid in the first vessel.

13. The method of claim 11, wherein removing, in situ, the at least one of at least one volatile byproduct and at least one nonvolatile byproduct comprises distilling, in situ, the at least one volatile byproduct.

14. The method of claim 11, wherein removing, in situ, the at least one of at least one volatile byproduct and at least one nonvolatile byproduct comprises adding water to the solution comprising 1,3,5-trialkoxy-2,4,6-trinitrobenzene and the at least one of at least one volatile byproduct and at least one nonvolatile byproduct.

15. The method of claim 11, further comprising exposing trinitrophloroglucinol to an acidic, aqueous solution in the first vessel.

16. The method of claim 11, further comprising exposing trinitrophloroglucinol to an acidic, aqueous solution in the second vessel.

17. The method of claim 11, further comprising distilling, in situ, water from the second vessel.

18. The method of claim 11, further comprising removing excess alkoxylating agent from the second vessel.

19. The method of claim 18, wherein removing excess alkoxylating agent from the second vessel comprises reacting the excess alkoxylating agent with water.

20. A method of producing 1,3,5-triamino-2,4,6-trinitrobenzene, comprising:
nitrating phloroglucinol to produce a reaction mixture comprising trinitrophloroglucinol;
exposing the trinitrophloroglucinol to an aqueous solution of hydrochloric acid to produce acid wet trinitrophloroglucinol;
removing, in situ, water from the acid wet trinitrophloroglucinol;
reacting the trinitrophloroglucinol with triethyl orthoformate to form a solution comprising 1,3,5-triethoxy-2,4,6-trinitrobenzene;
removing, in situ, byproducts from the solution comprising 1,3,5-triethoxy-2,4,6-trinitrobenzene; and
reacting the 1,3,5-triethoxy-2,4,6-trinitrobenzene with an aminating agent.

21. The method of claim 20, wherein exposing the trinitrophloroglucinol to an aqueous solution of hydrochloric acid to produce acid wet trinitrophloroglucinol comprises exposing the trinitrophloroglucinol to the aqueous solution comprising from approximately 0.5% by weight to approximately 25% by weight of hydrochloric acid.

22. The method of claim 20, wherein removing, in situ, water from the acid wet trinitrophloroglucinol comprises azeotropically distilling the water from a second vessel.

23. The method of claim 20, wherein reacting the trinitrophloroglucinol with triethyl orthoformate to form a solution comprising 1,3,5-triethoxy-2,4,6-trinitrobenzene comprises reacting the trinitrophloroglucinol with triethyl orthoformate in a second vessel.

24. The method of claim 20, wherein removing, in situ, byproducts from the solution comprising 1,3,5-triethoxy-2,4,6-trinitrobenzene comprises distilling, in situ, at least one volatile byproduct from a second vessel.

25. The method of claim 20, wherein removing, in situ, byproducts from the solution comprising 1,3,5-triethoxy-2,4,6-trinitrobenzene comprises adding water to the solution comprising 1,3,5-trialkoxy-2,4,6-trinitrobenzene to remove at least one nonvolatile byproduct.

* * * * *